(12) United States Patent
Andrieu et al.

(10) Patent No.: US 9,863,048 B2
(45) Date of Patent: Jan. 9, 2018

(54) SYNTHESIS AND USE OF BIOBASED IMIDAZOLIUM CARBOXYLATES

(71) Applicant: UNIVERSITÉ DE BOURGOGNE, Dijon (FR)

(72) Inventors: Jacques Andrieu, Dijon (FR); Charles Devillers, Dijon (FR); Guillaume de Robillard, Chevigny Saint Sauveur (FR)

(73) Assignee: UNIVERSITÉ DE BOURGOGNE, Dijon (FR)

( * ) Notice: Subject to any disclaimer, the term of this patent is extended or adjusted under 35 U.S.C. 154(b) by 554 days.

(21) Appl. No.: 14/323,950

(22) Filed: Jul. 3, 2014

(65) Prior Publication Data
US 2016/0002796 A1    Jan. 7, 2016

(51) Int. Cl.
| | |
|---|---|
| *C25B 3/00* | (2006.01) |
| *C25B 3/04* | (2006.01) |
| *C01B 31/20* | (2006.01) |
| *C07D 233/90* | (2006.01) |
| *C07D 233/58* | (2006.01) |
| *C07D 233/54* | (2006.01) |

(52) U.S. Cl.
CPC ............ *C25B 3/04* (2013.01); *C01B 31/20* (2013.01); *C07D 233/54* (2013.01); *C07D 233/58* (2013.01); *C07D 233/90* (2013.01)

(58) Field of Classification Search
CPC ............ C25B 3/00; C25B 3/02; C25B 3/04
USPC ........................................ 205/440, 442, 413
See application file for complete search history.

(56) References Cited

FOREIGN PATENT DOCUMENTS

CN        101078129 A        11/2007

OTHER PUBLICATIONS de Robillard et al., "Electrosynthesis of Imidazolium Carboxylates", Org. Lett. (no month, 2013), vol. 15, Nov. 17, pp. 4410-4413.*

Arduengo, A.J.,"Looking for stable carbenes: the difficulty in starting anew", Acc. Chem. Res., vol. 32, No. 11, Aug. 1999, pp. 913-921.

Kuhn et al. Z. Naturforsch, "Synthesis and properties of 1, 3-diisopropyl-4, 5-dimethylimidazolium-2 carboxylate A stable carbene adduct of carbon dioxide [1]" 1999, 54 b, p. 427. (English abstract provided).

Holbrey et al., "1,3-Dimethylimidazolium-2-carboxylate: the unexpected synthesis of an ionic liquid precursor and carbene-CO2 adduct", J. Chem. Commun., 2003, pp. 28-29.

Nonnenmacher, M. et al., "X-ray crystal structures of $10\pi$—and $14\pi$—electron pyrido-annelated N-heterocyclic carbenes", Chem. Commun., 2006, pp. 1378-1380.

De Robillard, G. et al, "Electrosynthesis of imidazolium carboxylates", Organic Letters, vol. 15, No. 17, Sep. 2013, pp. 4410-4413.

Feroci, M. et al., "Stability and CO2 capture ability of electrogenerated N-heterocyclic carbene in parent 1-butyl-3-methylimidazolium ionic liquid (BMIm-X): the role of X-", Chemelectrochem, vol. 1, No. 8, Mar. 2014, pp. 1407-1414.

\* cited by examiner

*Primary Examiner* — Edna Wong
(74) *Attorney, Agent, or Firm* — Young & Thompson

(57) ABSTRACT

The present invention relates to a new method for preparation of biobased imidazolium salts and derivatives thereof; in particular, for the preparation of imidazolium hydrogenooxalate. The present invention also relates to uses of imidazolium hydrogenooxalate salts, especially as a precursor of imidazolium carboxylate compounds. The present invention also refers to a green electrochemical process providing imidazolium compounds, especially imidazolium carboxylate compounds. Especially, the invention refers to a one-compartment electrochemical cell and its use for the preparation of imidazolium carboxylate compounds of formula (II):

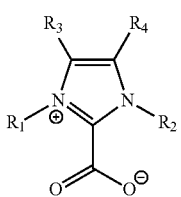

Formula (II)

4 Claims, No Drawings

SYNTHESIS AND USE OF BIOBASED IMIDAZOLIUM CARBOXYLATES

FIELD OF THE INVENTION

The present invention relates to a new method for preparation of biobased imidazolium salts and derivatives thereof; in particular, for the preparation of imidazolium hydrogenooxalate. The present invention also relates to uses of imidazolium hydrogenooxalate salts, especially as a precursor of imidazolium carboxylate compounds. The present invention also refers to a green electrochemical process providing imidazolium compounds, especially imidazolium carboxylate compounds. Especially, the invention refers to a one-compartment electrochemical cell and its use for the preparation of imidazolium carboxylate compounds.

BACKGROUND OF INVENTION

One of the most important challenges of our century concerns reduction of the negative effects of human activities on the Environment. The development of new technologies thus owes integrate a responsible approach of both environmental and societal management to build a sustainable industry, in particular in the chemical industries.

Thus, in the latest century was born the concept of "green chemistry", namely a chemistry worried of implementing principles of reduction or limited generation of harmful substances for the Environment since its sources.

For instance, in pharmaceutical and chemical industry, nitrogen heterocyclic compounds, mainly N-heterocyclic carbenes (NHC), are commonly used in many applications such as ligands for organometallics catalysts, organic catalyst, material and drug syntheses, therapeutics or electrochemistry. However, these high value-added products have been prepared until now, by energy-consuming processes that use reagents with strong negative environmental impacts. Furthermore, their handling is still sensitive: the used conditions of NHC synthesis lead to highly explosive atmosphere and finally, to high professional risks. Consequently, it is necessary to develop both eco-friendly and safe processes in this chemical field.

Currently, a large majority of N-heterocyclic carbenes are synthesized from their corresponding imidazolium salts by deprotonation with a strong base (n-BuLi, tBuOK, NaH), which usually requires special conditions (low temperature, inert atmosphere; Arduengo, A. J., *Acc. Chem. Res.*, 1999, 32, p 913). Numerous works are devoted to the synthesis of an intermediate stable masked carbenes allowing regenerating in situ free carbenes by thermal activation. Among these compounds, imidazolium 2-carboxylate compound is particularly interesting in that it allows spontaneous carbon dioxide delivery.

Until now, two chemicals pathways have been reported to prepare imidazolium 2-carboxylate. The first one (method A) consists of deprotonation of imidazolium salt compound at low temperature and under inert atmosphere in order to provide a free intermediate carbene which then, will react by contacting itself with a solution comprising carbon dioxide (Kuhn, N. et al. *Naturforsch* 1999, 54b, 427):

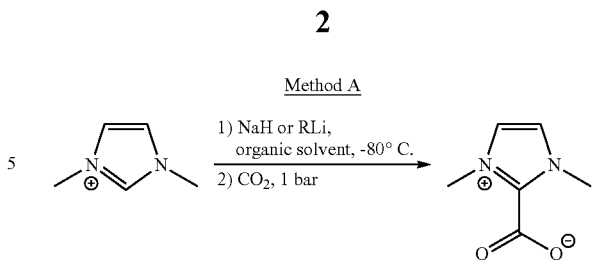

Method A

During this reaction, a very reactive carbene is provided, constraining the experimenter to work at cryogenic temperatures for avoiding any pyrophoric risk.

The second (method B) refers to a <<one-pot>> reaction of both N-methylation and C-carboxylation of N-monosubstituted imidazole precursor using dimethylcarbonate (DMC) as a reagent (Holbrey, J. et al. *Chem. Commun.* 2003, 28):

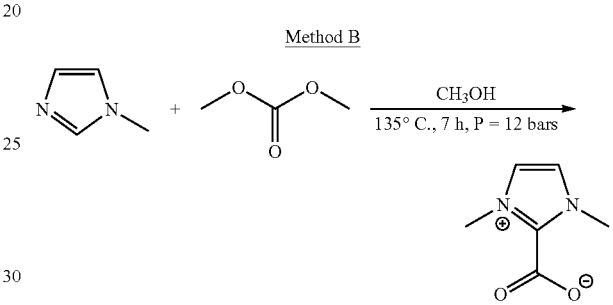

Method B

Contrary to the first method, this latest chemical way requires high temperature and pressure conditions that limit methylation (with DMC) reaction on the remaining unsubstituted-N atom and needs specific experimental material.

The aim is thus to provide imidazolium carboxylate compounds by a green process easy to implement, safe and allowing having products without toxic subproducts.

Surprisingly, the Applicant has discovered a process and a new electrochemical device for preparation of imidazolium 2-carboxylate overcoming the drawbacks previously described. Especially, the Applicant has further discovered a method for preparation of new imidazolium salts, particularly imidazolium hydrogenooxalate salts from bio-based reagents, useful for providing bio-sourced imidazolium 2-carboxylate compounds by a more eco-friendly electrochemical way.

DEFINITIONS

In the present invention, the following terms have the following meanings:
"Imidazolium salt" refers to any salt comprising an imidazolium moiety and a negative counter-ion.
"Imidazolium carboxylate salt" refers to any salt comprising an imidazolium moiety and a counter-ion having at least one carboxylate group.
"Imidazolium carboxylate compound" or "imidazolium 2-carboxylate" refers to one chemical compound comprising an imidazolium ring bearing one carboxylate group in position 2 of the imidazolium ring.
"about" preceding a figure means plus or less 10% of the value of said figure.
"alkyl" refers to compound of formula $C_nH_{2n+1}$, wherein n is a number greater than or equal to 1. Generally, alkyl groups of this invention comprise from 1 to 14 carbon atoms. Alkyl groups may be linear or branched and may be substituted. Examples of alkyl groups are methyl, ethyl, n-propyl, i-propyl, butyl and its isomers (e.g. n-butyl, i-butyl and t-butyl); pentyl and its isomers, hexyl and its isomers.

"alkene" refers to any linear or branched hydrocarbon chain having at least one double bond, preferably 2 to 12 carbon atoms.

"alkyne" refers to any linear or branched hydrocarbon chain having at least one triple carbon bond; preferably 2 to 12 carbon atoms.

"aryl" refers to any polyunsaturated, aromatic hydrocarbyl group having a single ring (i.e. phenyl) or multiple aromatic rings fused together (e.g. naphtyl) or linked covalently, typically containing 6 to 50 atoms; preferably 6 to 10, wherein at least one ring is aromatic.

"heteroaryl" refers to aryl group having at least one atom that is not carbon or hydrogen; preferably, said atom is selected from N, S, P or O.

"cycloalkyl" refers to a cyclic alkyl group, that is to say, a monovalent, saturated, or unsaturated hydrocarbyl group having 1 or 2 cyclic structure. Cycloalkyl includes all saturated hydrocarbon groups containing 1 to 2 rings, including monocyclic or bicyclic groups. Cycloalkyl groups may comprise 3 or more carbon atoms in the ring and generally, according to this invention comprise from 3 to 10, more preferably from 3 to 8 carbon atoms still more preferably from 3 to 6 carbon atoms. The further rings of multi-ring cycloalkyls may be either fused, bridged and/or joined through one or more spiro atoms. Examples of cycloalkyl groups include but are not limited to cyclopropyl, cyclobutyl, cyclopentyl, cyclohexyl.

"cycloalkene" refers to a cyclic alkene group that is to say, a monovalent, saturated, or unsaturated hydrocarbyl group having 1 or 2 cyclic structure. Cycloalkene includes all unsaturated hydrocarbon groups containing 1 to 2 rings, including monocyclic or bicyclic groups. Cycloalkene groups may comprise 3 or more carbon atoms in the ring and generally, according to this invention comprise from 3 to 10, more preferably from 3 to 8 carbon atoms still more preferably from 3 to 6 carbon atoms. The further rings of multi-ring cycloalkene may be either fused, bridged and/or joined through one or more spiro atoms. Examples of cycloalkene groups include but are not limited to cyclopropenyl, cyclobutenyl, cyclopentenyl, cyclohexenyl.

"heteroalkyl" refers to refers to alkyl group having at least one atom that is not carbon or hydrogen; preferably, said atom is selected from N, S, P or O.

"heterocycloalkyl" refers to a cycloalkyl group having at least one atom that is not carbon or hydrogen; preferably, said atom is selected from N, S, P or O.

"oxalyl" or "oxalo" or "diacyl" refers to a compound bearing a vicinal diketone group, e.g. two C=O groups, side-by-side.

"aldehyde" refers to an organic compound comprising at least one formyl group of general formula R—CHO, wherein R represents a substituted or unsubstituted group selected from aryl or alkyl group. In the present invention, aldehyde is preferably paraformaldehyde or formaldehyde.

DETAILED DESCRIPTION

Process of Manufacture and Device

This invention applies to a process for preparation of isolable imidazolium carboxylate compounds of general formula II:

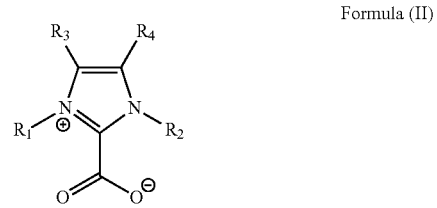

Formula (II)

wherein:

$R^1$ or $R^2$: may be identical or different and each is selected from the group of H, aryl, alkyl, alkene, alkyne, cycloalkyl, cycloalkene, heteroalkyl, heteroaryl or heterocycloalkyl group; optionally substituted by at least one group selected from aryl, hydroxyl, oxo, nitro, amido, carboxy, amino, cyano, alkoxy, alkyl, alkene, alkyne, cycloalkyl, cycloalkene, heteroalkyl, heteroaryl or heterocycloalkyl group; preferably $R^1$ and $R^2$ are identical; more preferably, $R^1$ and $R^2$ are both alkyl chain substituted by an alkyl or aryl group;

$R^3$ or $R^4$: may be identical or different and each is selected from the group of H, aryl, alkyl, alkene, alkyne, alkoxy, cycloalkyl, cycloalkene, heteroalkyl, heteroaryl or heterocycloalkyl group; optionally substituted by at least one group selected from aryl, hydroxyl, oxo, nitro, amido, carboxy, amino, cyano, alkoxy, alkyl, alkene, alkyne, cycloalkyl, cycloalkene, heteroalkyl, heteroaryl or heterocycloalkyl group; preferably $R^3$ and $R^4$ are identical; more preferably, $R^3$ and $R^4$ are both H, alkyl group or aryl group;

and derivatives thereof, comprising:
  introducing a supporting electrolyte comprising imidazolium salts, which may be a ionic liquid, in an electrochemical cell;
  synthesizing imidazolium carboxylate compounds by electrochemical reaction in one step and at room temperature; and wherein the electrochemical cell does not comprise two compartments.

In one embodiment, $R^1$ and $R^3$ may represent one fused substituent selected from the group of aryl, heteroaryl, cycloalkyl, cycloalkane or heterocycloalkyl; optionally substituted by at least one group selected from aryl, hydroxyl, oxo, nitro, amido, carboxy, amino, cyano, alkoxy, alkyl, alkene, alkyne, cycloalkyl, cycloalkene, heteroalkyl or heterocycloalkyl group; preferably fused $R^1$ and $R^3$ are one aryl group optionally substituted by at least one group selected from hydroxyl, oxo, nitro, amido, carboxy, amino, cyano, alkoxy, alkyl, alkene or alkyne.

In one embodiment, $R^2$ and $R^4$ may represent one fused substituent selected from the group of aryl, heteroaryl, cycloalkyl, cycloalkane or heterocycloalkyl; optionally substituted by at least one group selected from aryl, hydroxyl, oxo, nitro, amido, carboxy, amino, cyano, alkoxy, alkyl, alkene, alkyne, cycloalkyl, cycloalkene, heteroalkyl or heterocycloalkyl group; preferably fused $R^2$ and $R^4$ are one aryl group optionally substituted by at least one group selected from hydroxyl, oxo, nitro, amido, carboxy, amino, cyano, alkoxy, alkyl, alkene or alkyne.

In one embodiment, $R^3$ and $R^4$ may represent one fused substituent selected from the group of aryl, heteroaryl, cycloalkyl, cycloalkane or heterocycloalkyl; optionally substituted by at least one group selected from aryl, hydroxyl, oxo, nitro, amido, carboxy, amino, cyano, alkoxy, alkyl, alkene, alkyne, cycloalkyl, cycloalkene, heteroalkyl or heterocycloalkyl group; preferably fused $R^3$ and $R^4$ are one aryl group optionally substituted by at least one group selected from hydroxyl, oxo, nitro, amido, carboxy, amino, cyano, alkoxy, alkyl, alkene or alkyne.

According to one embodiment, the electrochemical cell is divided or not; preferably the electrochemical cell comprises three compartments; more preferably the electrochemical cell comprises only one compartment. According to one embodiment, the compartments were separated by a porous glass frit or other ion conducting bridge.

According to one embodiment, the electrochemical cell further comprises a carbon dioxide source.

According to one embodiment, the electrochemical cell comprises at least two electrodes; preferably the electrochemical cell comprises three electrodes: one working electrode, one reference electrode and one auxiliary electrode.

For electrochemical reduction, the working electrode may be a suitable conductive electrode selected from at least one Al, Au, Ag, Boron doped diamond, C, Cd, Co, Cr, Cu, Cu alloys, Ga, Hg, In, Ir, Mg, Mo, Nb, Ni, Ni alloys, lead oxide, Li—Fe alloys, Os, Pb, Pd, Pt, Rh, Ru, Sn, Sn alloys, Ti, V, W, Zn, elgiloy, austenitic steel, duplex steel, ferritic steel, martensitic steel, stainless steel, degenerately doped p-Si, degenerately doped p-Si:As and degenerately p-Si: B; preferably the electrode is C, Pt or stainless steel.

According to one embodiment, the auxiliary electrode may be a suitable conductive electrode selected from at least one Al, Au, Ag, Boron doped diamond, C, Cd, Co, Cr, Cu, Cu alloys, Ga, Hg, In, Ir, Mg, Mo, Nb, Ni, Ni alloys, lead oxide, Li—Fe alloys, Os, Pb, Pd, Pt, Rh, Ru, Sn, Sn alloys, Ti, V, W, Zn, elgiloy, austenitic steel, duplex steel, ferritic steel, martensitic steel, stainless steel, degenerately doped p-Si, degenerately doped p-Si:As and degenerately p-Si: B; preferably the electrode is C, Pt or stainless steel.

According to one embodiment, the reference electrode is selected from saturated calomel electrode (SCE), silver-silver chloride electrode (Ag/AgCl) or $Ag/AgNO_3$; preferably the reference electrode is SCE.

According to one embodiment, the electrical potential applied at the working electrode ranges from about 0 volt to −4 volts versus the SCE; preferably the electrical potential ranges from −1.5 volts to −3 volts versus the SCE.

According to one embodiment, the current during the process of invention is applied or not; preferably the current is applied and the current density ranges from 1 $mA/m^2$ to 4 $kA/m^2$.

According to one embodiment, the supporting electrolyte is selected from solid or liquid compounds, water or organic liquid comprising ionic liquids, salts such as $Na_2SO_4$, KCl, $NaNO_3$, NaCl, NaF, $KClO_4$, $K_2SiO_3$, $CaCl_2$, ions such as a H cation, a Li cation, a Na cation, a K cation, a Rb cation, a Cs cation, an ammonium cation, an alkylammonium cation, a F anion, a Cl anion a Br anion, a I anion, an At anion, an alkyl amine, borates, carbonates, nitrites, nitrates, phosphates, polyphosphates, perchlorates, silicates, sulfates and tetralkyl ammonium salt, organic solvents or carboxylic acids. According to one preferred embodiment the electrolyte is tetrabutylammonium hexafluorophosphate ($TBAPF_6$), tetraethylammonium hexafluorophosphate ($TEAPF_6$), $I^-$, $BF4^-$ or imidazolium salts.

According to one embodiment, the supporting electrolyte is selected from biosourced compounds.

According to one embodiment, the supporting electrolyte is used at a concentration ranging from 0.01 mol/L to a saturated solution; preferably is the highest concentration.

According to one embodiment, the solvent used in the process of invention is selected from organic solvents; preferably polar and aprotic solvents, ionic liquids, bio-based solvents or mixed solvents; more preferably is dimethylformamide, acetonitrile or bio-based solvents.

It is understood by room temperature in the process of the invention a temperature ranging from 15° C. to 40° C.; preferably the temperature is 25° C.

According to one embodiment, the faradaic yield of desired products ranges from 50% to 100%.

In this process, compounds with formula (II) are obtained by electro-reduction of imidazolium salts as shown in scheme 1:

Scheme 1. Method of synthesis for compounds with formula (II).

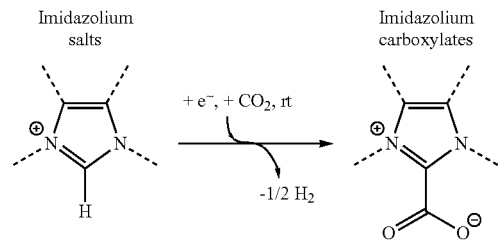

In the same time, the electrolyte or the counter-ion of imidazolium salts used in the process of the invention is oxidized. As the great majority of counter-ions or electrolytes are halo compounds, the final products of the electrosynthesis are often contaminated and need a purification step. In order to improve this process, the Applicant have worked for optimization of the oxidation step; especially, in order to provide a process wherein the subproducts of oxidation step are easy to eliminate at the end of the reaction and allowing to provide final products with a high purity degree.

Surprisingly, the Applicant has found that the use of carboxylate ion as counter-ion of imidazolium salts allows achieving these goals and enables to provide an electrochemical material easier to use for industrial purposes.

Consequently, the invention also relates to a process for preparation of imidazolium carboxylate compounds of general formula (II):

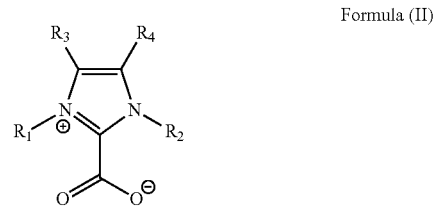

Formula (II)

wherein $R^1$, $R^2$, $R^3$ or $R^4$ are as defined above,
comprising:
introducing a supporting electrolyte comprising imidazolium carboxylate salts in an electrochemical cell; preferably a solution of imidazolium hydrogenooxalate salts;

synthesizing imidazolium 2-carboxylate by electrochemical reaction in one step and at room temperature.

According to one embodiment, the electrochemical cell is divided or not. According to a very preferred embodiment, the electrochemical cell comprises only one compartment.

According to one embodiment, the electrochemical cell comprises at least two electrodes; preferably the electrochemical cell comprises one working electrode, one reference electrode and one auxiliary electrode; more preferably the electrochemical cell does not comprise any reference electrode.

For electrochemical reduction and oxidation, the electrodes are identical or not and may be a suitable conductive electrode selected from at least one Al, Au, Ag, Boron doped diamond, C, Cd, Co, Cr, Cu, Cu alloys, Ga, Hg, In, Ir, Mg, Mo, Nb, Ni, Ni alloys, lead oxide, Li—Fe alloys, Os, Pb, Pd, Pt, Rh, Ru, Sn, Sn alloys, Ti, V, W, Zn, elgiloy, austenitic steel, duplex steel, ferritic steel, martensitic steel, stainless steel, degenerately doped p-Si, degenerately doped p-Si:As and degenerately p-Si: B; preferably the electrode is C, Pt or stainless steel.

According to one preferred embodiment, the products of the oxidation step do not contaminate the products of the reduction step.

According to one embodiment, the process of the invention is led under anhydrous conditions or not; preferably under anhydrous conditions.

According to one embodiment, the supporting electrolyte is the starting material; preferably the supporting electrolyte is halogen-free imidazolium salt; more preferably is selected from the group of imidazolium hydrogenooxalate salts.

According to one embodiment, the subproducts of the oxidation reaction during the electrolysis are non-toxic compounds, easy to remove from the final reaction medium; preferably at least one subproduct is a gaseous compound; more preferably is carbon dioxide.

According to one embodiment, the solvent used in the process of invention is selected from organic solvents; preferably from aprotic and highly ionic solvents; more preferably the solvent is dimethylformamide, acetonitrile or a polar bio-based solvent.

According to one embodiment, the electrochemical cell further comprises a carbon dioxide source.

According to one embodiment, the temperature used in the process of the invention is ranging from 15° C. to 40° C.; preferably the temperature is 25° C.

According to one embodiment, the faradaic yield of desired products ranges from 50% to 100%.

In particular, the invention concerns a one-compartment electrochemical cell comprising:
a cathode;
an anode;
a halogen-free supporting electrolyte comprising compounds of general formula (I'):

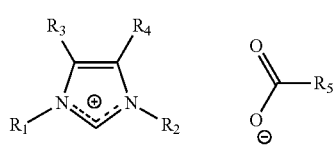

Formula (I')

and derivatives thereof, wherein:
$R^1$ or $R^2$: may be identical or different and each is selected from the group of H, aryl, alkyl, alkene, alkyne, cycloalkyl, cycloalkene, heteroalkyl or heterocycloalkyl group; optionally substituted by at least one group selected from aryl, hydroxyl, oxo, nitro, amido, carboxy, amino, cyano, alkoxy, alkyl, alkene, alkyne, cycloalkyl, cycloalkene, heteroalkyl or heterocycloalkyl group; preferably $R^1$ and $R^2$ are identical; more preferably, $R^1$ and $R^2$ are both alkyl chain substituted by an alkyl or aryl group;

$R^3$ or $R^4$: may be identical or different and each is selected from the group of H, aryl, alkyl, alkene, alkyne, alkoxy, cycloalkyl, cycloalkene, heteroalkyl or heterocycloalkyl group; optionally substituted by at least one group selected from aryl, hydroxyl, oxo, nitro, amido, carboxy, amino, cyano, alkoxy, alkyl, alkene, alkyne, cycloalkyl, cycloalkene, heteroalkyl or heterocycloalkyl group; preferably $R^3$ and $R^4$ are identical; more preferably, $R^3$ and $R^4$ are both H or alkyl group;

$R^5$ is selected from the group of H, aryl, alkyl, alkene, alkyne, alkoxy, cycloalkyl, cycloalkene, heteroalkyl or heterocycloalkyl group; optionally substituted by at least one group selected from aryl, hydroxyl, oxo, nitro, amido, carboxy, amino, cyano, alkoxy, alkyl, alkene, alkyne, cycloalkyl, cycloalkene, heteroalkyl or heterocycloalkyl group; preferably $R^5$ is H or a carboxy group.

For electrochemical reduction and oxidation, the electrodes are identical or not and may be a suitable conductive electrode selected from at least one Al, Au, Ag, Boron doped diamond, C, Cd, Co, Cr, Cu, Cu alloys, Ga, Hg, In, Ir, Mg, Mo, Nb, Ni, Ni alloys, lead oxide, Li—Fe alloys, Os, Pb, Pd, Pt, Rh, Ru, Sn, Sn alloys, Ti, V, W, Zn, elgiloy, austenitic steel, duplex steel, ferritic steel, martensitic steel, stainless steel, degenerately doped p-Si, degenerately doped p-Si:As and degenerately p-Si: B; preferably the electrode is C, Pt or stainless steel.

According to one embodiment, the halogen-free supporting electrolyte is selected from the group of imidazolium hydrogenooxalate salts of general formula (I):

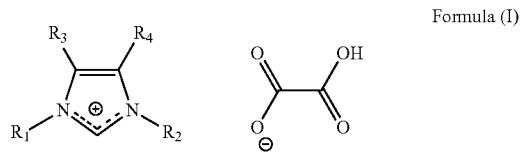

Formula (I)

wherein $R^1$, $R^2$, $R^3$ and $R^4$ are as defined in the general formula (I').

Formula (I) corresponds to the general formula (I') wherein $R^5$ is carboxyl group.

Imidazolium carboxylate salts of the present invention are more specifically represented by compounds of formula (Ia) and (Ib):

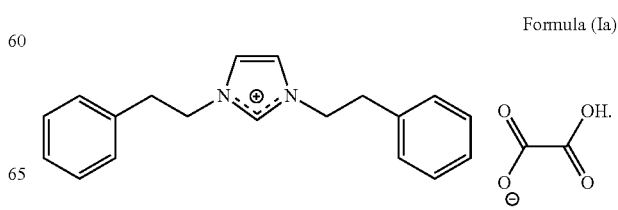

Formula (Ia)

Formula (Ib)

 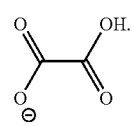

According to one preferred embodiment, the imidazolium salts are biobased compounds.

The invention relates also the use of the one-compartment electrochemical cell as described above for the preparation of imidazolium carboxylate compounds of general formula (II):

Formula (II)

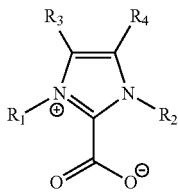

wherein $R^1$, $R^2$, $R^3$ and $R^4$ are as defined above.

According to one embodiment, the preparation of imidazolium carboxylate compounds is implemented in only one step.

According to one embodiment, the imidazolium salts are the only carbon dioxide source.

According to one embodiment, the products of the oxidation step do not contaminate the products of the reduction step.

According to one embodiment, the subproducts of the oxidation reaction during the electrolysis are non-toxic compounds, easy to remove from the final reaction medium; preferably at least one subproduct is a gaseous compound; more preferably is carbon dioxide.

According to one embodiment, the use of the one-compartment electrochemical cell is led under anhydrous conditions or not; preferably under anhydrous conditions.

According to one embodiment, the use of the one-compartment electrochemical cell is implemented at room temperature.

The invention also relates to a process for preparation of imidazolium carboxylate salts of general formula I':

Formula (I')

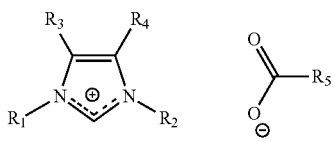

and derivatives thereof, wherein $R^1$, $R^2$, $R^3$, $R^4$ and $R^5$ are as defined above;
comprising:
mixing a solution of biobased primary amines, a carboxylic acid compound an aldehyde compound and an oxalyl compound.

The method for preparation of compounds with formula (I') is shown in scheme 2:

Scheme 2. Synthesis method for compounds with formula (I')

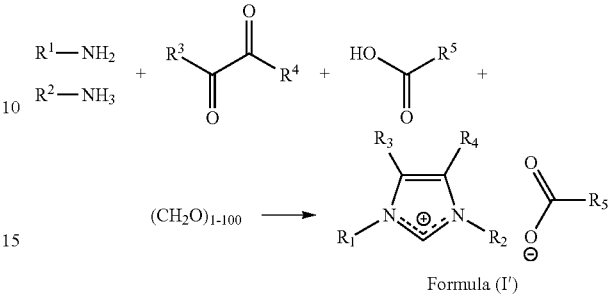

Formula (I')

According to one embodiment, the reagents used in the process of the invention are selected from commercially available chemical compounds or bio-based compounds; preferably bio-based compounds; more preferably the reagents used in the process of the invention are extracted from biomass.

According to one preferred embodiment, the primary amines used in the process of the invention are bio-based compounds selected from the group comprising spermidine, putrescine, spermine, mercaptoethylamine, histamine, phenylethylamine, ethanolamine, serotonine, cadaverine; preferably phenylethylamine or isobutylamine.

According to one preferred embodiment, the primary amines are compounds extracted by physical, chemical or enzymatical way.

According to one embodiment, the oxalyl compounds used in the process of the invention are selected from any organic compound bearing an oxalyl group; preferably the oxalyl compound is ethanedial, 2,3-butanedione or benzil.

According to one embodiment, the aldehyde compound used in the process of the invention is selected from any organic compound bearing a formyl group; preferably the aldehyde compound is formaldehyde or paraformaldehyde.

According to one preferred embodiment, the carboxylic acid compounds used in the process of the invention are selected from the group of organic compounds bearing at least one carboxyl group; preferably two carboxyl groups.

According to one embodiment, the carboxylic acid compounds used in the process of the invention have a pKa measured in water below 7; preferably below 5; more preferably, below 4.

According to one embodiment, the dicarboxylic acid compounds used in the process of the invention have a $pKa_1$ measured in water below 2, preferably ranging from 0.8 to less than 2.

According to a very preferred embodiment, the carboxylic acid used in the process of the invention is oxalic or formic acid. In one embodiment, the oxalic acid may be extracted from starch, sawdust or cellulose.

According to one embodiment, the solvent is water or an organic solvent; preferably the solvent is benign for environment or a bio-based solvent.

According to one embodiment, the temperature used in the process of the invention is ranging from 0° C. to 150° C.; preferably the temperature is ranging from 25° C. to 80° C.

According to one embodiment, the molar ratio of carboxylic and oxalyl compounds is ranging from 0 to 1; preferably the molar ratio is 1.

In another aspect, the invention also relates to a cyclic process for delivering dioxide carbon stocked in a material, membrane support, solid or liquid, comprising the following reaction steps:

carbon dioxide delivering by contacting imidazolium carboxylate compound with oxalic acid or formic acid leading to synthesis of imidazolium hydrogeno-oxalate or imidazolium formate salt;

regeneration of imidazolium carboxylate compound by electrochemical process from imidazolium hydrogeno-oxalate or imidazolium formate salts obtained during the previous reaction step.

The method for delivering dioxide carbon includes the steps shown in scheme 3:

Scheme 3. Cyclic process for delivering $CO_2$ when oxalic acid is used.

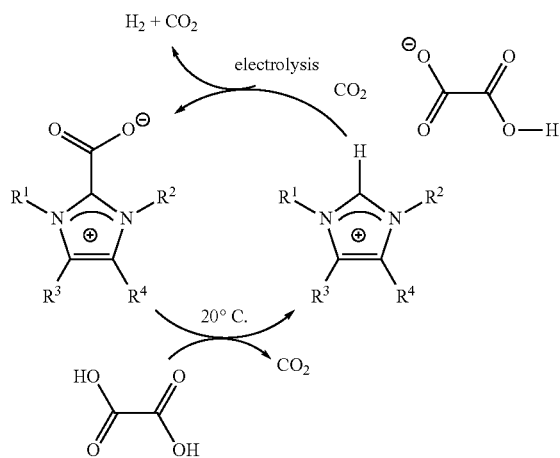

According to one embodiment, the temperature used during the dioxide carbon delivering step and/or the regeneration step is ranging from 15° C. to 80° C., preferably is about 20° C.

According to a one embodiment, the imidazolium hydrogenooxalate salts used in the process of invention are compounds of general formula (I):

Formula (I)

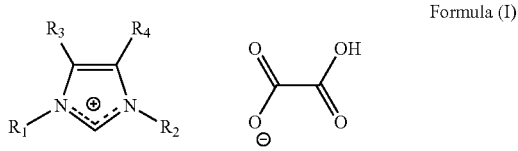

wherein $R^1$, $R^2$, $R^3$ and $R^4$ are as defined above.

According to one embodiment, the regeneration step is implemented in the one-compartment electrochemical cell as described above.

Compounds

The invention also relates to compounds with general formula (I'):

Formula (I')

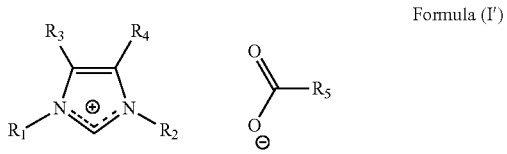

and derivatives thereof, wherein:

$R^1$ or $R^2$: may be identical or different and each is selected from the group of H, aryl, alkyl, alkene, alkyne, cycloalkyl, cycloalkene, heteroalkyl, heteroaryl or heterocycloalkyl group; optionally substituted by at least one group selected from aryl, hydroxyl, oxo, nitro, amido, carboxy, amino, cyano, alkoxy, alkyl, alkene, alkyne, cycloalkyl, cycloalkene, heteroalkyl, heteroaryl or heterocycloalkyl group; preferably $R^1$ and $R^2$ are identical; more preferably, $R^1$ and $R^2$ are both alkyl chain substituted by an alkyl or aryl group or $R^1$ and $R^2$ are both aryl group.

$R^3$ or $R^4$: may be identical or different and each is selected from the group of H, aryl, alkyl, alkene, alkyne, alkoxy, cycloalkyl, cycloalkene, heteroalkyl, heteroaryl or heterocycloalkyl group; optionally substituted by at least one group selected from aryl, hydroxyl, oxo, nitro, amido, carboxy, amino, cyano, alkoxy, alkyl, alkene, alkyne, cycloalkyl, cycloalkene, heteroalkyl, heteroaryl or heterocycloalkyl group; preferably $R^3$ and $R^4$ are identical; more preferably, $R^3$ and $R^4$ are both H or alkyl group;

$R^5$ is selected from the group of H, aryl, alkyl, alkene, alkyne, alkoxy, cycloalkyl, cycloalkene, heteroalkyl or heterocycloalkyl group; optionally substituted by at least one group selected from aryl, hydroxyl, oxo, nitro, amido, carboxy, amino, cyano, alkoxy, alkyl, alkene, alkyne, cycloalkyl, cycloalkene, heteroalkyl or heterocycloalkyl group; preferably $R^5$ is H or a carboxyl group.

According to one preferred embodiment, the compounds according to the invention have the general formula (I):

Formula (I)

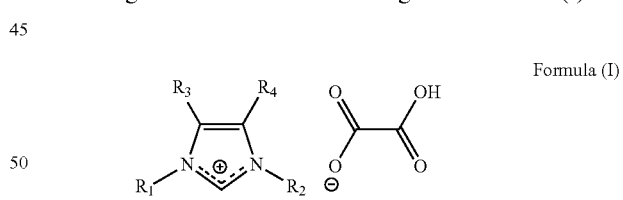

wherein $R^1$, $R^2$, $R^3$ and $R^4$ are as defined in the general formula (I').

According to one embodiment, the preferred compounds of formula (I) are 1,3-di-(phenylethyl)imidazolium hydrogenooxalates salts (formula Ia):

Formula (Ia)

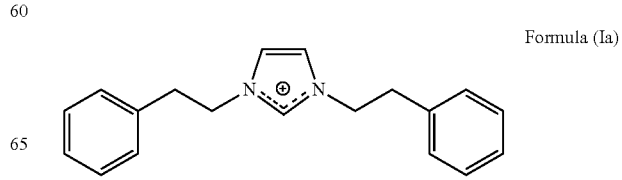

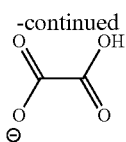

or 1,3-di(isobutyl)imidazolium hydrogenooxalate salts (formula Ib):

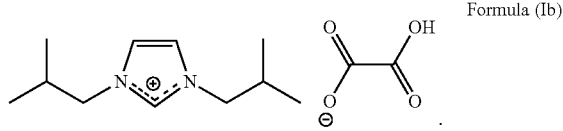

Uses of Compounds According to the Invention

As mentioned previously, compounds of general formula (I') according to this invention can act as catalysts or precursors for different kind of uses.

According to one embodiment, compounds with formula (I') may be used as catalysts. In particular, they may be used in polymer or organic chemistry.

According to one embodiment, compounds with formula (I'), and particularly formula (I), (Ia) or (Ib) according to the invention, may be used as ionic liquid precursor.

According to one embodiment, compounds with formula (I'), and particularly formula (I), (Ia) or (Ib) according to the invention, may be used as imidazolium 2-carboxylate precursor.

According to another embodiment, compounds with formula (I') according to the invention, may be used as anti-infectious and/or anti-bacterial agents.

As mentioned previously, compounds of general formula (II) according to this invention can act as catalysts or precursors for different kind of uses.

According to one embodiment, compounds with formula (II) may be used as catalysts. In particular, they may be used in polymer or organometallic and organic chemistry.

According to one embodiment, compounds with formula (II) may be used as ionic liquid precursor with a high purity.

According to one embodiment, compounds with formula (II) may be used as safe carbenes precursor.

EXAMPLES

The present invention will be better understood after reading the following examples that provide non-limitative illustrations of the invention.

Chemistry Examples

Solvents, reagents and starting materials were purchased from well-known chemical suppliers such as for example Sigma Aldrich, Acros Organics, VWR Int., Sopachem or Polymer labs.

Abbreviations
ACN or MeCN: Acetonitrile,
$CHCl_3$: chloroform
eq: Equivalent,
g: Grams,
h: Hours,
HRMS: High-resolution Mass Spectrometry
L: Liters,
M: mol/L min or mn: Minutes,
mL: Milliliters,
mg: Milligrams,
MW: Micro-waves,
μl: Microliters,
mol: Moles,
mmol: Millimoles,
RT: Room temperature,
THF: Tetrahydrofuran,
tBu: tert-Butyl
TMS: trimethylsilyl,
Y: Yield.

Example 1: Synthesis of Imidazolium Hydrogenooxalates Salts from Bio-Based Primary Amines 1.1 Preparation of 1,3-di-(2-phenylethyl)imidazolium hydrogenooxalates salts

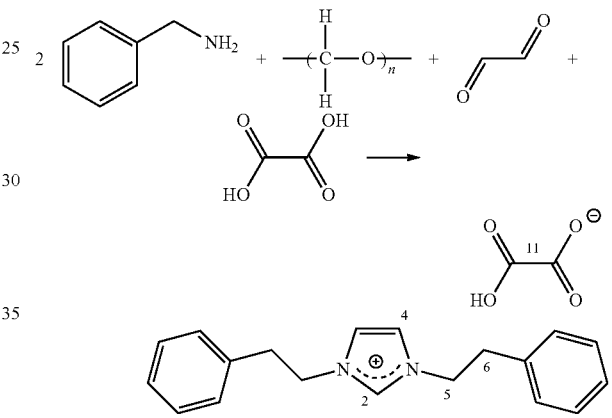

2-phenylethylamine (8.85 mL, 70.4 mmol) was added to a suspension of paraformaldehyde (2.11 g, 70.4 mmol) in toluene (100 mL) which was cooled at 0° C. with a water bath. Afterwards the reaction mixture was stirred for 30 min and then cooled to 0° C. Another equivalent of 2-phenylethylamine (8.85 mL, 70.4 mmol), oxalic acid (6.34 g, 70.4 mmol) and water (25 mL) were added. The cooling bath was removed and the solution allows stirring for 2 hours. Then glyoxal (40 wt % solution in water, 8.1 mL, 70.4 mmol) was added. The mixture was stirred for 2 hours at 110° C. and water was removed by a Dean-Stark apparatus. The resulting dark brown solution was stirred overnight. All volatile material was removed in vacuo and the brown residue was dissolved in a minimum of acetonitrile, filtered to remove the solids and precipitated with THF. A brown solid was obtained and it was purified by recrystallization in a mixture of chloroform/THF to give 20.6 g (80%) of an off white powder.

$^1$H NMR (MeOD, 300 MHz, 298 K) δ (ppm) 8.81 (H2, s, 1H), 7.42 (H4, d, 2H), 7.32-7.20 ($H_{méta-para}$, m, 6H), 7.12 ($H_{ortho}$, m, 4H), 4.43 (H5, t, 4H), 3.10 (H6, t, 4H); $^{13}$C NMR (MeOD, 75 MHz, 298 K) δ (ppm) 169.1 (C11), 137.8 (C2), 129.9 (C), 129.8 (C), 128.2 (C), 123.7 (C), 123.6 (C), 51.86 (C5), 37.2 (C6). HRMS (ESI-MS) m/z calcd. For $C_{19}H_{21}N_2$ [M]$^+$: 277.16976, found: 277.16993. Elemental analysis: Calc. for $C_{21}H_{23}N_2O_4$: C, 68.65; H, 6.31; N, 7.62. Found: C, 69.10; H, 6.50; N, 7.92.

1.2 Preparation of 1,3-di-(isobutyl)imidazolium hydrogenooxalates salts

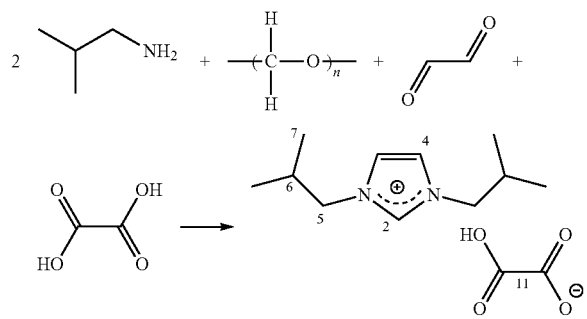

Isobutylamine (10 mL, 101 mmol) was added to a suspension of paraformaldehyde (3.05 g, 102 mmol) in toluene (100 mL) which was cooled at 0° C. with a water bath. Afterwards the reaction mixture was stirred for 30 min and then cooled to 0° C. Another equivalent of isobutylamine (10 mL, 101 mmol), oxalic acid (9.06 g, 101 mmol) and water (25 mL) were added. The cooling bath was removed and the solution allows stirring for 2 hours. Then glyoxal (40 wt % solution in water, 11.5 mL, 100 mmol) was added. The mixture was stirred for 2 hours at 110° C. and water was removed by a Dean-Stark apparatus. The resulting dark brown solution was stirred overnight. All volatile material was removed in vacuo and the brown residue was dissolved in a minimum of acetonitrile, filtered to remove the solids and precipitated with diethyl ether. A brown solid was obtained and it was purified by recrystallization in a mixture of chloroform/THF to give 18.4 g (68%) of an off white powder.

$^1$H NMR (CDCl$_3$, 300 MHz, 298 K) δ (ppm) 10.65 (H11, s, 1H), 8.77 (H2, s, 1H), 7.30 (H4, d, 2H), 4.14 (H5, d, 4H), 2.13 (H6, h, 2H), 0.91 (H7, d, 12H); $^{13}$C NMR (CDCl$_3$, 75 MHz, 298 K) δ (ppm) 165.16 (C11), 139.86 (C2), 122.08 (C4), 56.78 (C5), 29.61 (C6), 19.50 (C7). HRMS (ESI-MS) m/z calcd. For C$_{11}$H$_{21}$N$_2$ [M]$^+$: 181.16993, found: 181.16998. Elemental analysis: Calc. for C$_{13}$H$_{23}$N$_2$O$_4$: C, 57.55; H, 8.54; N, 10.32. Found: C, 57.41; H, 8.58; N, 10.61.

Example 2: Electrosynthesis of Imidazolium Carboxylate Salts from Imidazolium Halide Salts

2.1. General Comments

Solvents were dried according to standard procedures and saturated with argon prior to use. 1-methylbenzimidazole (Alfa-Aesar, 99%) and imidazo[1,5-a]pyridine (TCI, >98%) were obtained from commercial suppliers and used without further purifications. 1-methylimidazole (Fluka puriss, 99%) and dimethyl carbonate (Sigma-Aldrich, 99%) were distilled before utilization.

NMR spectra were recorded using a BRUKER 600 MHz Avance II, 500 MHz Avance II or 300 MHz Bruker Avance III NanoBay spectrometer. $^1$H and $^{13}$C {$^1$H}NMR spectra were calibrated to TMS on the basis of the relative chemical shift of the solvent as an internal standard.
Electrochemistry Conditions All manipulations were performed using Schlenk techniques at room temperature (T=20° C.±3° C.). The supporting electrolyte (tetraethylammonium or tetrabutylammonium hexafluorophosphate) was degassed under vacuum before use and then dissolved to a concentration of 0.1 M. Voltammetric analyses were carried out in a standard three-electrode cell, with an Autolab PGSTAT 302 N potentiostat, connected to an interfaced computer that employed Electrochemistry Nova software. The reference electrode was a saturated calomel electrode (SCE) separated from the analyzed solution by a sintered glass disk filled with the background solution. The auxiliary electrode was a platinum wire separated from the analyzed solution by a sintered glass disk filled with the background solution. For all voltammetric measurements, the working electrode was a platinum electrode disk (Ø=1 mm) In these conditions, when operating in dimethylformamide (0.1 M TBAPF$_6$), the formal potential for the ferrocene (+10) couple was found to be +0.32 V vs. SCE. When operating in CH$_3$CN (0.1 M TEAPF$_6$ and 0.1M TBAPF$_6$) the formal potential for the ferrocene (+/0) couple was found to be +0.40 V vs. SCE.

Bulk electrolyses were performed in a cell with three compartments separated with glass frits of medium porosity with an Amel 552 potentiostat coupled with an Amel 721 electronic integrator. A platinum wire spiral (l=50 cm, Ø=1 mm) was used as the working electrode, a platinum plate as the counter electrode and a saturated calomel electrode as the reference electrode.

2.2. General Procedure

Electrolyses were carried out by bubbling of carbon dioxide (atmospheric pressure), into 30 mL of solvent containing 0.1 M of supporting electrolyte and the imidazolium salt in a three compartment cell under vigorous stirring at ambient temperature and at controlled potential. Electrolyses were stopped after an uptake of 1.1-1.5 faraday per mol of imidazolium. After removing the solvent, the product was washed with 3×20 mL of THF and dried under vacuum.

2.3. Synthesis of the Starting Material: Compounds 3H$^+$, BF$_4^-$ and 4H$^+$, BF$_4^-$ Synthesis of 3H$_+$, BF4$_-$

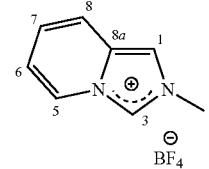

Imidazo[1,5-a]pyridine (2.000 g, 16.93 mmol) and [(Me)$_3$O][BF$_4$] (2.505 g, 16.94 mmol) were mixed at 0° C. in a solution of pre-cooled CH$_2$Cl$_2$ (20 mL). The solution was stirred overnight at room temperature. The suspension was filtered and the resulting solid was washed with cooled (0° C.) CH$_2$Cl$_2$ (3×10 mL). The solid was dried under vacuum (RT) to yield 54% of 3H$_+$, BF4$_-$ (2.034 g, 9.25 mmol)). $_1$H NMR (Acetone-d6, 300 MHz, 298 K): δ (ppm) 9.57 (s, H3, 1H), 8.62 (dd, 3J=7.1 Hz, 4J=0.9 Hz, H5, 1H), 8.18 (s, H1, 1H), 7.89 (dd, 3J=9.3 Hz, 4J=1.0 Hz, H8, 1H), 7.33 (ddd, 3J=9.3 Hz, 3J=6.9 Hz, 4J=0.9 Hz, H7, 1H), 7.22 (ddd, 1H, 3J=7.1 Hz, 3J=6.9 Hz, 4J=1.0 Hz, H6, 1H), 4.36 (s, CH3, 3H); $_{13}$C NMR (Acetone-d6, 75 MHz, 298 K): δ (ppm) 131.1 (C8a), 127.9 (C3), 125.7 (C7), 124.9 (C5), 119.0 (C8), 118.6 (C6), 115.6 (C1), 37.8 (CH3); HRMS (ESI-MS) m/z calcd. For $C_8H_9N_2$ [M]+: 133.07602, found: 133.07548; Elemental analysis: Calc. for $C_8H_9N_2BF_4$: C, 43.68; H, 4.12; N, 12.73. Found: C, 43.62; H, 4.12; N, 12.73.

Synthesis of 4H⁻, BF4⁻

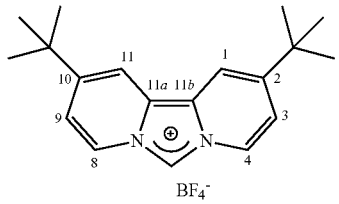

BF4⁻

The starting material was synthesized according to known procedures (Nonnenmacher, M.; Kunz, D.; Rominger, F.; Oeser, T. *Chem. Commun.* 2006, 1378.).

2.4. Preparation of 2-Methylpyrido[1,2-c]imidazolium-3-carboxylate (3CO₂)

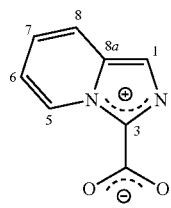

According to the general procedure, electrolysis of 3H⁺, BF4⁻ (47 mg, 0.21 mmol) was performed in dimethylformamide (TBAPF6 as supporting electrolyte) at −2.5 V/SCE. After an uptake of 1.14 faraday per mol of 3H⁺, BF4⁻ the electrolysis was stopped. After work-up, 66% of 3CO2 (25 mg, 0.14 mmol) were obtained.

¹H NMR (D₂O, 300 MHz, 298 K): δ (ppm) 9.22 (d, 3J=7.4 Hz, H5, 1H), 7.94 (s, H1, 1H), 7.78 (d, 3J=9.2 Hz, H8, 1H), 7.35 (dd, 3J=9.2 Hz 3J=6.8 Hz, H7, 1H), 7.21 (dd, 3J=7.4 Hz, 3J=6.8 Hz, H6, 1H), 4.38 (s, CH3, 3H); 13C NMR (D₂O, 75 MHz, 298 K): δ (ppm) 159.5 (CO2), 129.9 (C8a), 128.7 (C3), 126.2 (C7), 125.7 (C5), 119.0 (C6), 118.5 (C8), 116.9 (C1), 39.3 (CH3), assignment of ¹³C signals was done thanks to 2D ¹H, ¹³C HSQC and HMBC NMR techniques, in particular, in HMBC, cross peaks between H1 (7.94 ppm) and C8a (129.9 ppm), H8 (7.78 ppm) and C8a (129.9 ppm), H(CH3, 4.38 ppm) and C3 (128.7 ppm) were observed; moreover, one drop of CD³COCD³ was added for calibration (seen at 30.89 ppm); m.p.>150° C. (decomp.); FTIR (ATR) vmax/cm⁻¹: 3051, 1658, 1643, 1497, 1412, 1304, 1242, 995, 860, 798, 756; HRMS (ESI-MS) m/z calcd. For $C_9H_9N_2O_2^+$[M+H]⁺: 177.0659, found: 177.0651; for $C_9H_8N_2O_2Na^+$ [M+Na]⁺: 199.0478, found: 199.0469; Elemental analysis: Calc. for $C_9H_8N_2O_2$: C, 61.36; H, 4.58; N, 15.90. Found: C, 61.32; H, 4.57; N, 15.89.

2.5. Preparation of 2,10-Di-tert-butyl-dipyrido[1,2-c;2′,1′-e]imidazolium-6-carboxylate (4CO₂)

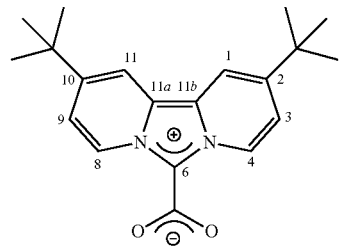 [SMILES: CC(C)(C)C1=CC2=C3C=C(C(C)(C)C)C=CN3C(C(O)O)N2C=C1]

According to the general procedure, electrolysis of 4H⁺, BF4⁻ (44 mg, 0.12 mmol) was performed in acetonitrile (TBAPF6 as supporting electrolyte) at −2.2 V/SCE. After an uptake of 1.5 faraday per mol of 4H⁺, BF4⁻ the electrolysis was stopped. After work-up, 84% of 4CO2 (33 mg, 0.10 mmol) were obtained.

¹H NMR (CDCl₃, 500 MHz, 298K): δ (ppm) 10.36 (dd, 3J=7.6 Hz, 5J=0.9 Hz, H4/H8, 2H), 7.99 (dd, 4J=1.8 Hz, 5J=0.9 Hz, H1/H11, 2H), 7.47 (dd, 3J=7.6 Hz, 4J=1.8 Hz, H3/H9, 2H), 1.45 (s, CH3, 18H); ¹³C NMR (125 MHz; CDCl3): δ=158.0 (CO2), 147.6 (C2/C10), 126.5 (C4/C8), 121.7 (C11a/C11b), 119.8 (C3/C9), 111.3 (C1/C11), 35.4 (C(CH3)3), 30.5 (CH3); assignment of ¹³C signals was done by 2D ¹H, ¹³C HSQC and HMBC NMR techniques. In particular, cross peaks between H (Me, 1.45 ppm) and C2/C10 (147.6 ppm) and H1/H11 (7.99 ppm) and C11a/C11b (121.7 ppm) were observed; despite all our efforts, the C6 carbon signal is not observed; m.p.>170° C. (decomp.); FTIR (ATR) vmax/cm⁻¹: 2959, 1648, 1539, 1273, 1195, 1050 (w), 891, 833, 802, 771; HRMS (ESI-MS) m/z calcd. For $C_{20}H_{24}N_2O_2Na^+$ [M+Na]⁺: 347.17300, found: 347.17223; Elemental analysis: Calc. for $C_{20}H_{24}N_2O_2$: C, 74.04; H, 7.46; N, 8.64. Found: C, 73.99; H, 7.46; N, 8.66.

Example 3: Electrosynthesis of Imidazolium Carboxylate Salts from Imidazolium Hydrogenooxalate Compounds 3.1. Synthesis of 1,3-diisobutylimidazolium carboxylate

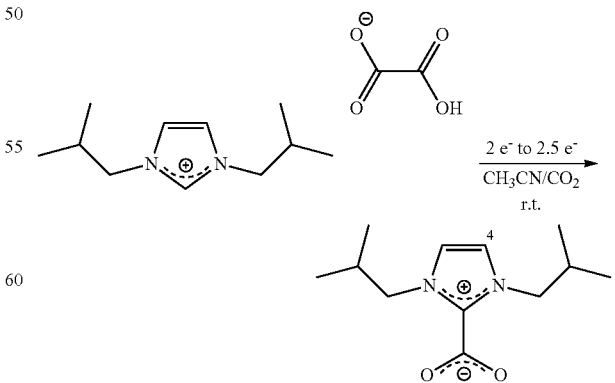

The electrolysis was performed in an electrochemical cell at one compartment under CO₂-atmosphere with 2 carbon electrodes (working electrode and auxiliary electrode) at applied current (from 15 mA to 50 mA) or at controlled potential (−2.8 V/SCE) with a reference electrode. All these experiments lead to imidazolium carboxylate compounds. After purification, the final product was dried affording 1,3-diisobutylimidazolium carboxylate in good yields. $^1$H NMR (CDCl$_3$, 500 MHz, 298K) δ (ppm) 7.03 (H$_{4/5}$, s, 2H), 4.35 (CH$_2$, d$^3$J=7.30 Hz, 4H), 2.17 (CH, m, 2H), 0.92 (CH$_3$, d $^3$J=6.38 Hz, 12H); $^{13}$C NMR (CDCl$_3$, 125 MHz, 298K) δ (ppm) 155.1 (CO$_2$), 143.9 (C2), 120.5 (C4/5), 56.8 (CH2), 29.8 (CH), 19.7 (CH3).

3.2. Synthesis of 1,3-diphenylethyllimidazolium carboxylate

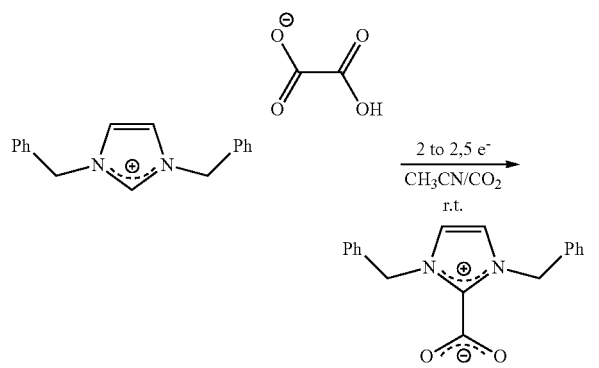

The electrolysis was performed in an electrochemical cell at one compartment under CO$_2$-atmosphere with 2 carbon electrodes (working electrode and auxiliary electrode) and at applied current (10 mA). This experiment leads to imidazolium carboxylate. After purification, the final product was dried affording 1,3-diphenylethyllimidazolium carboxylate in good yields.

The results show that the electrolysis of imidazolium hydrogenooxalate in one compartment on carbon support and under CO$_2$ atmosphere allows preparation of imidazolium carboxylate compound.

Example 4: CO$_2$-Delivery from Imidazolium Carboxylate Compounds

An example of CO$_2$ delivery experiment is given with an imidazolium carboxylate with formula (II) with R$^1$=R$^2$=CH$_3$ and R$^3$=R$^4$=H:

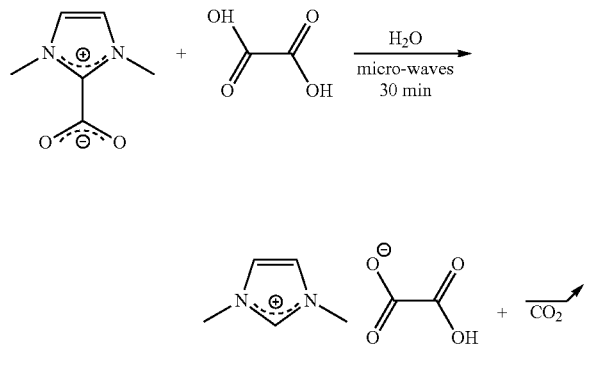

The invention claimed is:
1. A method of preparing imidazolium carboxylate compounds of general formula II:

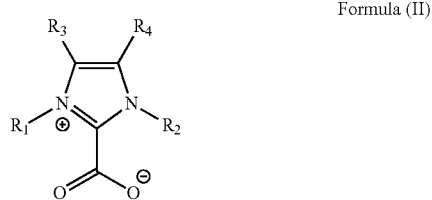

Formula (II)

and derivatives thereof, wherein:
R$^1$ and R$^2$ are each independently selected from the group consisting of H, aryl, alkyl, alkene, alkyne, cycloalkyl, cycloalkene, heteroalkyl, heteroaryl and heterocycloalkyl group; and R$^1$ and R$^2$ are each optionally substituted by at least one group selected from the group consisting of aryl, hydroxyl, oxo, nitro, amido, carboxy, amino, cyano, alkoxy, alkyl, alkene, alkyne, cycloalkyl, cycloalkene, heteroalkyl, heteroaryl and heterocycloalkyl group;

R$^3$ and R$^4$ are each independently selected from the group consisting of H, aryl, alkyl, alkene, alkyne, alkoxy, cycloalkyl, cycloalkene, heteroalkyl, heteroaryl and heterocycloalkyl group; and R$^3$ and R$^4$ are each optionally substituted by at least one group selected from the group consisting of aryl, hydroxyl, oxo, nitro, amido, carboxy, amino, cyano, alkoxy, alkyl, alkene, alkyne, cycloalkyl, cycloalkene, heteroalkyl, heteroaryl and heterocycloalkyl group;

said method comprising:
introducing in an electrochemical cell, a supporting electrolyte comprising imidazolium carboxylate salts of formula (I'):

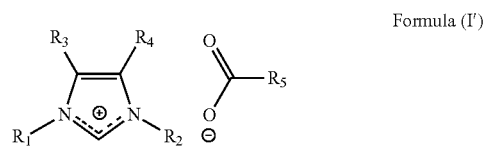

Formula (I')

and derivatives thereof, wherein:
R$^1$ and R$^2$ are each independently selected from the group consisting of H, aryl, alkyl, alkene, alkyne, cycloalkyl, cycloalkene, heteroalkyl, heteroaryl and heterocycloalkyl group; and R$^1$ and R$^2$ are each optionally substituted by at least one group selected from the group consisting of aryl, hydroxyl, oxo, nitro, amido, carboxy, amino, cyano, alkoxy, alkyl, alkene, alkyne, cycloalkyl, cycloalkene, heteroalkyl, heteroaryl and heterocycloalkyl group;

R$^3$ and R$^4$ are each independently selected from the group consisting of H, aryl, alkyl, alkene, alkyne, alkoxy, cycloalkyl, cycloalkene, heteroalkyl, heteroaryl and heterocycloalkyl group; and R$^3$ and R$^4$ are each optionally substituted by at least one group selected from the group consisting of aryl, hydroxyl, oxo, nitro, amido, carboxy, amino, cyano, alkoxy, alkyl, alkene, alkyne, cycloalkyl, cycloalkene, heteroalkyl, heteroaryl and heterocycloalkyl group; and $R^5$ is selected from the group consisting of H, aryl, alkyl, alkene, alkyne, alkoxy, cycloalkyl, cycloalkene, heteroalkyl, heteroaryl and heterocycloalkyl group; optionally substituted by at least one group selected from the group consisting of aryl, hydroxyl, oxo, nitro, amido, carboxy, amino, cyano, alkoxy, alkyl, alkene, alkyne, cycloalkyl, cycloalkene, heteroalkyl, heteroaryl and heterocycloalkyl group; and synthesizing said imidazolium carboxylate compounds of formula (II) by electrochemical reaction in one step and at room temperature;

wherein the electrochemical cell does not comprise two compartments.

2. The method of claim 1, wherein the imidazolium salt is selected from imidazolium hydrogeno-oxalate salts and derivatives thereof.

3. The method of claim 1, wherein the electrochemical cell is constituted by only one compartment.

4. The method of claim 1, wherein the electrochemical cell further comprises a carbon dioxide source.

\* \* \* \* \*